(12) United States Patent
Rutenberg et al.

(10) Patent No.: US 10,561,674 B2
(45) Date of Patent: Feb. 18, 2020

(54) PROCESSES FOR THE PREPARATION OF PHOSPHOLIPID-ENRICHED DAIRY PRODUCTS AS NEUTRACEUTICALS FOR THE FORMULATION OF FUNCTIONAL FOODS

(71) Applicant: Lipogen Ltd., Haifa (IL)

(72) Inventors: David Rutenberg, Haifa (IL); Ilan Perry, Moshav Bat Shlomo (IL)

(73) Assignee: Lipogen Ltd., Haifa (IL)

( * ) Notice: Subject to any disclaimer, the term of this patent is extended or adjusted under 35 U.S.C. 154(b) by 226 days.

(21) Appl. No.: 15/230,494

(22) Filed: Aug. 8, 2016

(65) Prior Publication Data

US 2016/0339044 A1    Nov. 24, 2016

Related U.S. Application Data

(60) Continuation-in-part of application No. 14/728,555, filed on Jun. 2, 2015, now abandoned, which is a division of application No. 13/783,317, filed on Mar. 3, 2013, now abandoned.

(51) Int. Cl.

| | |
|---|---|
| A61K 31/685 | (2006.01) |
| A23C 9/152 | (2006.01) |
| A23C 9/13 | (2006.01) |
| A23D 9/013 | (2006.01) |
| A23L 29/00 | (2016.01) |
| A23D 7/01 | (2006.01) |
| A23C 19/093 | (2006.01) |
| A23G 9/32 | (2006.01) |
| A23G 1/36 | (2006.01) |
| A23J 7/00 | (2006.01) |
| A61K 31/661 | (2006.01) |
| A23C 19/076 | (2006.01) |
| A23L 33/115 | (2016.01) |
| A23C 19/055 | (2006.01) |
| A61K 31/6615 | (2006.01) |

(52) U.S. Cl.
CPC .......... *A61K 31/685* (2013.01); *A23C 9/1315* (2013.01); *A23C 9/1528* (2013.01); *A23C 19/055* (2013.01); *A23C 19/0765* (2013.01); *A23C 19/093* (2013.01); *A23D 7/01* (2013.01); *A23D 7/011* (2013.01); *A23D 7/013* (2013.01); *A23D 9/013* (2013.01); *A23G 1/36* (2013.01); *A23G 9/327* (2013.01); *A23J 7/00* (2013.01); *A23L 29/05* (2016.08); *A23L 33/115* (2016.08); *A61K 31/661* (2013.01); *A61K 31/6615* (2013.01); *A23V 2002/00* (2013.01)

(58) Field of Classification Search
CPC .................................................... A61K 31/33
USPC ................................................ 514/183, 170
See application file for complete search history.

(56) References Cited

U.S. PATENT DOCUMENTS

| | | |
|---|---|---|
| 2,945,869 A | 7/1960 | Meyer et al. |
| 3,544,605 A | 12/1970 | Betzing et al. |
| 3,798,246 A | 3/1974 | Shimazaki |
| 4,166,823 A | 9/1979 | Siertz |
| 4,235,793 A | 11/1980 | Betzing |
| 4,425,276 A | 1/1984 | Gunther |
| 4,443,378 A | 4/1984 | Gunther |
| 4,452,743 A | 6/1984 | Gunther |
| 4,528,139 A | 7/1985 | Napp |
| 5,453,523 A | 9/1995 | Weete et al. |
| 8,231,922 B2 | 7/2012 | Burling et al. |

FOREIGN PATENT DOCUMENTS

| | | |
|---|---|---|
| EP | 0057989 A2 | 8/1982 |
| EP | 0997074 A1 | 3/2000 |
| EP | 1106181 A1 | 6/2001 |

OTHER PUBLICATIONS

Horn AF et al, Agriculture 2012, 2, 359-375 http://orbit.dtu.dk/fedora/objects/orbit:116505/datastreams/file_7c7bf9e7-eed4-4f36-b924-1aa7d81b8bed/co.
Szuhaj, Lecithins: Sources, Manugfacture & Uses, The American Oil Chemists Society, Jan. 1, 1989, p. 19, 159-160.
Cherry, J.P., in Szuhaj, B.F. (ed.), Lecithins: Sources, Manufacture & Uses, The American Oil Chemists' Society, Champaign, 1989, pp. 16-31.
Schmidt J.C., et al, In Szuhaj, B.F. and List (ed.), American Oil Chemists' Socitey, Champaign, 1985, pp. 203-211.
Szuhaj, Lecithin production and utilization. Journal of the American Oil Chemists' Society, Feb. 1983, vol. 60, Issue 2, 00 306-309.
Van Nieuwenhuyzen et al, "Effects of lecithins and proteins on the stability of emulsions", Lipid/Fett 100.7 (1998): 282-291.
Anonymous, "Flavored Milk", DataBase GNPD [online] Mintel, XP002720782, Database accession No. 1318363, 2010.
Anonymous, "Traditional Egg Nog", DataBase GNPD [online] Mintel, XP002720783, Database accession No. 1695214, 2011.

*Primary Examiner* — Layla Soroush
(74) *Attorney, Agent, or Firm* — Reuven K. Mouallem; FlashPoint IP Ltd.

(57) ABSTRACT

The present invention discloses processes for the preparation of phospholipid-enriched dairy products as nutraceuticals for the formulation of functional foods, the processes include the steps of: combining a non-dairy-based PL-containing material, having phosphatidylserine (PS) and/or phosphatidic acid (PA) in the PL-containing material, wherein the PS and/or PA is derived in part from an enzymatically-processed lecithin as a PS-calcium and/or -magnesium salt and/or a PA-calcium and/or-magnesium salt via transphosphatidylation with phospholipase D in the presence of L-serine and a calcium and/or magnesium salt, with water and an oil component to form a paste; removing an excess amount of the water from the paste to form a PL-oil solution; and mixing the PL-oil solution with a dairy component, thereby obtaining a PL-enriched dairy product. Alternatively, the PL-oil solution has a weight-to-weight (w-w) concentration of at least about 0.01% of a residual amount of the water to the PL-containing material.

13 Claims, No Drawings

PROCESSES FOR THE PREPARATION OF PHOSPHOLIPID-ENRICHED DAIRY PRODUCTS AS NEUTRACEUTICALS FOR THE FORMULATION OF FUNCTIONAL FOODS

CROSS REFERENCE TO RELATED APPLICATIONS

This patent application is a continuation-in-part (CIP) application of, and claims priority to, U.S. patent application Ser. No. 14/728,555 filed on Jun. 2, 2015, U.S. patent application Ser. No. 13/783,317 filed on Mar. 3, 2013, and claims priority to Israel Patent Application No. 223373 filed on Dec. 2, 2012, and which are hereby incorporated by reference in their entirety.

FIELD AND BACKGROUND OF THE INVENTION

The present invention relates to processes for the preparation of phospholipid-enriched dairy products as nutraceuticals for the formulation of functional foods.

Phospholipids (PLs) are ubiquitous biological substances, making up the membrane material in most cells in both plants and animals. PLs have been used extensively in pharmaceutical compositions, nutritional compounds, and functional foods. As an example, the importance of phosphatidylserine (PS) as a functional ingredient is supported by the US FDA's qualified health claims in which the usage of phosphatidylserine was related to the reduction of cognitive dysfunction and dementia in the elderly.

PLs can be used as a nutraceutical (including a medication, a medical food, a functional food, and a dietary supplement) in various food formulations, drinks, tablets, and bars containing concentrated, nutritional, and/or dietary ingredients. The addition of PLs to dairy formulations is exacerbated by undesirable attributes of a finished product such as unpleasant taste, non-homogenous consistency, unattractive appearance, and/or poor fractionation stability, among others.

U.S. Pat. No. 8,231,922 by Burling et al. (hereinafter referred to as Burling '922) recites a bovine-milk-derived, phosphatidylserine source of natural composition having excellent dispersibility and organoleptic as well as physical stability using PS-enriched milk fractions. As disclosed in Burling '922, natural milk is a poor source of PS, with only ~27 mg PS/liter in whole milk and ~10 mg PS/liter in skim milk. Buttermilk provides a better source of PS, with cream-churned buttermilk containing ~130 mg PS/liter, while butter-oil-derived buttermilk contains ~250 mg PS/liter. In a society concerned with reducing dietary fat intake, the loss of naturally-occurring PS during the skimming process of removing fat from milk leaves the nutritional benefit substantially depleted. The skimming process is thought to deplete the naturally-occurring PLs in the milk.

Burling '922 further discloses test results for a milk-added, buttermilk-derived PS (2.0% PS) being physically-, chemically-, and organoleptically-stable, with no precipitation. Milk-added, soy-derived PS (21% and 62% from Enzymotec, Israel) was found to be physically unstable, with 70% of the PS precipitating and settling after one week. Moreover, the milk-added, soy-derived PS was found to be organoleptically unstable, acquiring an unpleasant off-taste typical for soy that made the milk almost undrinkable. All comparative formulations were standardized to provide 100 mg of PS for a 200 ml serving of a skim-milk based drink.

Salt-free phospholipids as described by B. F. Szuhaj (see p. 157 in *Lecithins: Sources, Manufacture & Uses, American Oil Chemists' Society (AOCS) Press*, Champaign, Ill., 1989; *Lecithins, American Oil Chemists' Society (AOCS) Press*, Champaign, Ill., 1985; and "Lecithin Production and Utilization," *J. American Oil Chemists' Society*, pp. 306-309, 1983) which can be isolated and concentrated through selective fractionation are well-known in the art. However, such methods are less desirable due to economic considerations given the relatively low yields of industrially-important PLs such as PS and PA. While enzymatically-processed lecithin as described by Burling '922 can provide relatively high yields, the negative impact of the calcium salts on solubility in water-based solutions make such industrial routes unsuitable for practical production of PS- and PA-enriched dairy products.

Burling '922 emphasizes the challenges posed to formulating water-based products (which inherently include all dairy-based formulations) because of the need to activate the enzyme with calcium in such procedures, the PS often ends as a scarcely dispersible Ca salt. Moreover, Burling '922 points out that another problem associated with the head-group exchange procedure is the small residues of phospholipase D enzyme activity, which lead to instability of PS in water-based liquid systems. Furthermore, PL fractions tend to produce a very unpleasant taste (i.e., organoleptically unstable) in water-based systems.

Schmidt et al. (in *Lecithins, AOCS Press*, Champaign, Ill., pp. 203-211, 1985) describes hydrolyzed lecithins in which selective hydrolysis is accomplished by employing enzymes for fatty-acid cleavage. Szuhaj (in *Lecithins: Sources, Manufacture & Uses, AOCS Press*, Champaign, Ill., p. 160, 1989) suggests that such a water-hydration method would ameliorate organoleptic problems in salt-free forms of PS; however, such methods were not related to the calcium salts of PS or PA. Moreover, such suggestions would not be readily discernible as applicable to such calcium salts as they are counter to the teachings of Burling '922.

It would be desirable to have processes for the preparation of PL-enriched dairy products as nutraceuticals for the formulation of functional foods, including non-dairy-derived PS and/or PA. Such processes would, inter alia, overcome the limitations mentioned above.

SUMMARY OF THE INVENTION

It is the purpose of the present invention to provide processes for the preparation of PL-enriched dairy products as nutraceuticals (including medications, medical foods, functional foods, nutritional supplement, and dietary supplements) for the formulation of functional foods.

In the interest of clarity, the term "nutraceutical" is specifically defined for use herein to refer to any edible substance that is used in a medication, medical food, functional food, nutritional supplement, a pharmaceutical supplement, or dietary supplement, and provides medical and/or health benefits, including the prevention and treatment of disease.

Furthermore, it is noted that the term "exemplary" is used herein to refer to examples of embodiments and/or implementations, and is not meant to necessarily convey a more-desirable use-case. Similarly, the terms "alternative" and "alternatively" are used herein to refer to an example out of an assortment of contemplated embodiments and/or implementations, and is not meant to necessarily convey a more-desirable use-case. Therefore, it is understood from the above that "exemplary" and "alternative" may be applied herein to multiple embodiments and/or implementations. Various combinations of such alternative and/or exemplary embodiments are also contemplated herein.

Embodiments of the present invention provide processes for the preparation of PL-enriched dairy products as nutraceuticals for the formulation of functional foods. Such PL enrichment can serve as a nutraceutical ingredient for supplemental, dairy formulations. Such enriched dairy products include, but are not limited to, nutraceutical formulations of milk, milk chocolate, milk-ingredient supplemented products (e.g. enriched milk ingredients used in a powdered coffee or cocoa formulation), ice cream, dairy drinks, yoghurt, processed cheeses, cottage cheeses, dairy spreads, powdered dairy products, and nutritional dairy bars.

Therefore, according to the present invention, there is provided for the first time a process for the preparation of phospholipid-enriched (PL-enriched) dairy products as nutraceuticals for the formulation of functional foods, the process including the steps of: (a) combining a non-dairy-based PL-containing material, having phosphatidylserine (PS) in the PL-containing material, wherein the PS is derived in part from an enzymatically-processed lecithin as a PS-calcium and/or -magnesium salt via transphosphatidylation with phospholipase D in the presence of L-serine and a calcium and/or magnesium salt, with water and an oil component to form a paste; (b) removing an excess amount of the water from the paste to form a PL-oil solution; and (c) mixing the PL-oil solution with a dairy component, thereby obtaining a PL-enriched dairy product.

Alternatively, the PL-enriched dairy product has the form of at least one nutraceutical type selected from the group consisting of: a medication, a medical food, a medical drink, a functional food, a functional drink, a nutritional supplement, a pharmaceutical supplement, and a dietary supplement.

Alternatively, the PL-containing material includes at least one material selected from the group consisting of: a vegetal-derived lecithin, a non-vegetal-derived lecithin, a de-oiled lecithin, a native lecithin-oil solution, and an enzymatically-processed lecithin.

Alternatively, the oil component includes at least one material selected from the group consisting of: a carrier oil and a native oil fraction from a lecithin production process.

Alternatively, the step of combining is performed at a weight-to-weight (w-w) concentration of at least about 2% of the water to the PL-containing material.

Alternatively, the step of removing is performed by at least one process selected from the group consisting of: a heating procedure, a vacuum-distillation procedure, and a solvent-based phase-separation procedure.

Alternatively, the PL-oil solution has a weight-to-weight (w-w) concentration of at least about 0.01% of a residual amount of the water to the PL-containing material.

Alternatively, the PL-oil solution has a weight-to-weight (w-w) concentration of about 10-80% of the PL-containing material to the oil component.

Alternatively, the step of mixing includes at least one process selected from the group consisting of: a stirring procedure, a homogenizing procedure, and a pasteurizing procedure.

Alternatively, the PL-enriched dairy product has a weight-to-weight (w-w) concentration of up to about 50% of the PL-oil solution to the dairy component.

Alternatively, the PL-enriched dairy product is used in at least one product form selected from the group consisting of: a milk product, a chocolate product, a milk-ingredient supplemented product, an ice cream, a drink, a yoghurt, a processed cheese, a cottage cheese, a spread, a powdered dairy product, and a nutritional bar.

Alternatively, a PS concentration of the PS is at least about 10% weight-to-weight (w-w) out of the PL-containing material.

Most alternatively, the PS concentration is up to about 86% weight-to-weight (w-w) out of the PL-containing material.

According to the present invention, there is provided for the first time a process for the preparation of phospholipid-enriched (PL-enriched) dairy products as nutraceuticals for the formulation of functional foods, the process including the steps of: (a) combining a non-dairy-based PL-containing material, having phosphatidic acid (PA) in the PL-containing material, wherein the PA is derived in part from an enzymatically-processed lecithin as a PA-calcium and/or -magnesium salt via transphosphatidylation with phospholipase D in the presence of L-serine and a calcium and/or magnesium salt, with water and an oil component to form a paste; (b) removing an excess amount of the water from the paste to form a PL-oil solution; and (c) mixing the PL-oil solution with a dairy component, thereby obtaining a PL-enriched dairy product.

Alternatively, the PL-enriched dairy product has the form of at least one nutraceutical type selected from the group consisting of: a medication, a medical food, a medical drink, a functional food, a functional drink, a nutritional supplement, a pharmaceutical supplement, and a dietary supplement.

Alternatively, the PL-containing material includes at least one material selected from the group consisting of: a vegetal-derived lecithin, a non-vegetal-derived lecithin, a de-oiled lecithin, a native lecithin-oil solution, and an enzymatically-processed lecithin.

Alternatively, the oil component includes at least one material selected from the group consisting of: a carrier oil and a native oil fraction from a lecithin production process.

Alternatively, the step of combining is performed at a weight-to-weight (w-w) concentration of at least about 2% of the water to the PL-containing material.

Alternatively, the step of removing is performed by at least one process selected from the group consisting of: a heating procedure, a vacuum-distillation procedure, and a solvent-based phase-separation procedure.

Alternatively, the PL-oil solution has a weight-to-weight (w-w) concentration of at least about 0.01% of a residual amount of the water to the PL-containing material.

Alternatively, the PL-oil solution has a weight-to-weight (w-w) concentration of about 10-80% of the PL-containing material to the oil component.

Alternatively, the step of mixing includes at least one process selected from the group consisting of: a stirring procedure, a homogenizing procedure, and a pasteurizing procedure.

Alternatively, the PL-enriched dairy product has a weight-to-weight (w-w) concentration of up to about 50% of the PL-oil solution to the dairy component.

Alternatively, the PL-enriched dairy product is used in at least one product form selected from the group consisting of: a milk product, a chocolate product, a milk-ingredient supplemented product, an ice cream, a drink, a yoghurt, a processed cheese, a cottage cheese, a spread, a powdered dairy product, and a nutritional bar.

Alternatively, a PA concentration of the PA is at least about 15% weight-to-weight (w-w) out of the PL-containing material.

Most alternatively, the PA concentration is up to about 74% weight-to-weight (w-w) out of the PL-containing material.

These and further embodiments will be apparent from the detailed description and examples that follow.

DESCRIPTION OF THE ILLUSTRATIVE EMBODIMENTS

The present invention relates to processes for the preparation of PL-enriched dairy products as nutraceuticals for the formulation of functional foods. The principles and operation for preparing such PL-enriched dairy products, according to the present invention, may be better understood with reference to the accompanying description. Exemplary embodiments of the present invention are detailed below in the following exemplary processes.

EXAMPLE 1

A carrier oil (BERGABEST MCT Oil 60/40, Sternchemie GmbH & Co. KG) was combined with de-oiled lecithin (SternPur S P, Sternchemie GmbH & Co. KG) in a 5% weight-to-weight (w-w) concentration of water to lecithin to form a uniform paste. The paste was then heated under vacuum to remove the excess water to yield a lecithin-oil solution having at least about 0.01% residual water. It is noted that a solvent-based phase-separation method can be used instead of (or in addition to) the vacuum distillation procedure. The w-w concentration of water to lecithin of at least about 2% was found to be amenable to the process. The w-w concentration of lecithin to oil used was 60%. A w-w concentration of lecithin to oil range of 10-80% was found to be amenable to the process with regard to solubility and stability. Any source of lecithin can be used including vegetal-derived lecithin (e.g. soybean lecithin, sunflower lecithin, and rapeseed lecithin) and non-vegetal-derived lecithin (e.g. egg yolk lecithin and fish lecithin).

The lecithin-oil solution was then combined with skim milk at a concentration of 10% w-w lecithin-oil solution to milk. A range of up to about 50% w-w concentration was found to be amenable to the process with regard to solubility and stability. The mixture was then stirred gently. Vigorous stirring at this stage can result in layer fractionation which produces cream. The PL-fortified milk was then homogenized. It is thought that the natural components found in milk act as emulsifiers in the process. The PL-fortified milk was finally pasteurized to protect against spoilage.

A representative PL profile (weight fraction) for the PL-fortified milk included: phosphatidic acid (PA) at 7%, phosphatidylcholine (PC) at 49%, phosphatidylinositol (PI) at 14%, and phosphatidylethanolamine (PE) at 30%. Percentages represent the weight fraction of the relevant PL component out of a total PL content based on PS, PA, PC, PI, and PE combined.

EXAMPLE 2

Lecithin with its native oil fraction associated with the production of lecithin can also be used. The native lecithin-oil solution (Lecisoy, Cargill, Inc.) used had a concentration of lecithin to oil of 50% w-w. The concentration can be adjusted by either removing a portion of the oil fraction, or by adding a carrier oil. A range of 10-80% w-w concentration was found to be amenable to the process with regard to solubility and stability. Any source of lecithin can be used including vegetal-derived lecithin and non-vegetal-derived lecithin.

The lecithin-oil solution was then combined with whole milk at a concentration of 5% w-w. A range of up to about 50% w-w concentration was found to be amenable to the process with regard to solubility and stability. The mixture was then stirred gently. Vigorous stirring at this stage can result in layer fractionation which produces cream. The PL-fortified milk was then homogenized. The PL-fortified milk was finally pasteurized to protect against spoilage.

A representative PL profile (weight fraction) for the PL-fortified milk included: PA at 5%, PC at 42%, PI at 20%, and PE at 33%.

Enzymatically-Processed Lecithin

It is noted that the enzymatically-processed lecithin used in Examples 3-9 described below refers to a PS-calcium and/or -magnesium salt and/or a PA-calcium and/or -magnesium salt (among other PLs) produced via transphosphatidylation with lecithin and phospholipase D in the presence of L-serine and a calcium and/or magnesium salt (e.g., calcium chloride and/or magnesium chloride), which involves the exchange of the choline group in phosphatidyl choline for serine using phospholipase D as the active enzyme for the PS-production reaction to occur. Such enzymatic processing has been optimized to maximize the desired PL constituent (e.g., PS and/or PA). Further enhancement of the percentage of the PS and/or PA was achieved via fractionation. Thus, both the "semi-synthetic" route of enzymatic processing and fractionation can be fine-tuned in a continuous manner to achieve the desired amount of the PL constituents in suitable and stable dairy formulations up to the range tested (i.e., the complete, continuous range from about 10% up to about 88% for PS and up to about 74% for PA).

While ranges below 10% are certainly achievable (e.g., about 0.5%, 1%, 5%, and 8%) using such enzymatic processing, naturally-occurring amounts of desired PLs are within this low-end range as well. Moreover, moderate-level concentrations that are attainable (e.g., about 12%, 15%, 18%, and 20%) are not as industrially important; Examples 8 and 9 provide such formulations for establishing such viable, moderate-level concentrations. However, it is fully contemplated to be within the scope of the present invention that such low-level concentrations could serve as lower limits for producing suitable and stable dairy formulations. While Examples 3-9 described below provide experimental data for PS- and PA-rich formulations up to about 86% and 74%, respectively, it is certainly achievable and fully contemplated to obtain PS and PA formulations up to and including 100% through further selective fractionation as understood in the art. Thus, such formulations are within the scope of the present invention.

It is maintained that the other PLs present (i.e., PC, PE, and PI) are irrelevant to the matter of preparing such enriched dairy formulations. Firstly, inter alia, due to their relatively low concentrations in the formulations, any effect that such ancillary PLs could have would be minimized. Secondly, inter alia, such ancillary PLs have been shown to form soluble and stable dairy formulations; however, even the presence of low-level concentrations of so-called "salt-derived" PS and PA prevent traditional methods from being employed to ameliorate solubility and stability issues. Thirdly, inter alia, based on the prior art, clearly such "salt-derived" PS and PA pose the greatest challenge for producing soluble and stable dairy formulations; therefore, these aspects are only exacerbated by the presence of the "salt-derived" PS and PA.

Furthermore, based on the prior art and chemical intuition, it is clear that complications from producing such soluble and stable dairy formulations arising from calcium-based salts of PS and/or PA would equally present themselves in employing magnesium-based salts of PS and/or PA in the production process.

EXAMPLE 3 (PS- and PA-rich)

Enzymatically-processed lecithin can also be used, allowing the ratio of PL components (e.g. PS and PA) to be modified in order to obtain the desired type of nutraceutical product. Depending on the type of industrial PL material used, a minimum moisture content of at least about 0.01% w-w concentration of water to PL material may already be present in the commercially-available material. If the moisture content is below this threshold, then the procedure used in Example 1 can be followed. If the moisture content is above this threshold, then the procedure used in Example 2 can be followed.

A carrier oil (BERGABEST MCT Oil 60/40, Sternchemie GmbH & Co. KG) was combined with an industrial PL material (Lipogen PS20F, a PS-rich product produced by transphosphatidylation with lecithin and phospholipase D as described above from Lipogen Products (9000) Ltd., incorporated herein by reference in its entirety) having a sufficient moisture content to produce a PL-oil solution. The concentration of PLs to oil used was 65% w-w. A range of 10-80% w-w concentration was found to be amenable to the process with regard to solubility and stability.

The PL-oil solution was then combined with whole milk at a concentration of 2% w-w. A range of up to about 50% w-w concentration was found to be amenable to the process with regard to solubility and stability. The mixture was then stirred gently. Vigorous stirring at this stage can result in layer fractionation which produces cream. The PL-fortified milk was then homogenized. The PL-fortified milk was finally pasteurized to protect against spoilage.

A representative PL profile (weight fraction) based on $^{31}$P-NMR spectral data for the PL-fortified milk included: phosphatidylserine (PS) at 54%, PA at 18%, PC at 5%, PI at 18%, and PE at 5%, yielding a high-PS, suitable, and stable dairy formulation.

EXAMPLE 4 (PS-rich)

Enzymatically-processed lecithin used in formulation preparations similar to Example 3 were employed using Lipogen PS85P (a PS-rich product produced by transphosphatidylation with lecithin and phospholipase D as described above from Lipogen Products (9000) Ltd.), incorporated herein by reference in its entirety, to produce a high-PS, suitable, and stable dairy formulation. A representative PL profile (weight fraction) based on $^{31}$P-NMR spectral data for the PL-fortified milk included: PS at 88% (combined total of PS at 86.4% and LPS at 2%) and PA at 6% (combined total of PA at 4.9% and LPA at 1.1%).

EXAMPLE 5 (PA-rich)

Enzymatically-processed lecithin used in formulation preparations similar to Example 3 were employed using Lipogen PA70P (a PA-rich product produced by transphosphatidylation with lecithin and phospholipase D as described above from Lipogen Products (9000) Ltd.), incorporated herein by reference in its entirety, to produce a high-PA, suitable, and stable dairy formulation. A representative PL profile (weight fraction) based on $^{31}$P-NMR spectral data for the PL-fortified milk included: PA at 77% (combined total of PA at 74.1% and LPA at 2.9%), PI at 0.6%, and PE at 0.7% (combined total of PE, LPE, and APE).

EXAMPLE 6 (PA-rich)

Enzymatically-processed lecithin used in formulation preparations similar to Example 3 were employed using Lipogen PA70P (a PA-rich product produced by transphosphatidylation with lecithin and phospholipase D as described above from Lipogen Products (9000) Ltd.), incorporated herein by reference in its entirety, to produce a high-PA, suitable, and stable dairy formulation. A representative PL profile (weight fraction) based on $^{31}$P-NMR spectral data for the PL-fortified milk included: PA at 70.6% (combined total of PA at 68.7% and LPA at 1.9%), PI at 7.7%, and PE at 3.2%.

EXAMPLE 7 (PA-rich)

Enzymatically-processed lecithin used in formulation preparations similar to Example 3 were employed using Lipogen PA70P (a PA-rich product produced by transphosphatidylation with lecithin and phospholipase D as described above from Lipogen Products (9000) Ltd.), incorporated herein by reference in its entirety, to produce a high-PA, suitable, and stable dairy formulation. A representative PL profile (weight fraction) based on $^{31}$P-NMR spectral data for the PL-fortified milk included: PA at 77.8% (combined total of PA at 74.3% and LPA at 3.5%) and PI at 0.6%.

While the basis for the effects of the residual water employed in Examples 3-9 on the solubility of enzymatically-produced PS and/or PA in the PL-oil solution, and ultimately the PL-enriched dairy product, are purely speculative, and not the focus of the present invention, it may be that such residual water in the PL-oil solution mitigates the hydrophilic/hydrophobic properties of the enzymatically-produced PS and/or PA when combined with the water-based dairy component.

Such a water-based dairy component is known to be an emulsion having a hydrophilic water-phase, a hydrophobic fat-phase, and a protein portion that can behave like a surfactant. Furthermore, it is known that enzymatically-produced PS (as well as PA) is a poor surfactant. Therefore, mitigation of the hydrophilic/hydrophobic properties of the enzymatically-produced PS and/or PA containing a residual water component is likely the cause for the solubility, and hence the resulting, stable final product, observed in the experimental results.

EXAMPLE 8 (Moderate-level PS)

Enzymatically-processed lecithin used in formulation preparations similar to Example 3 were employed using Lipogen PAS15F (a PS and PA product produced by transphosphatidylation with lecithin and phospholipase D as described above from Lipogen Products (9000) Ltd.), incorporated herein by reference in its entirety, to produce a moderate-level PS, suitable, and stable dairy formulation. A representative PL profile (weight fraction) based on $^{31}$P-NMR spectral data for the PL-fortified milk included: PS at 10% with the remainder being other PLs.

EXAMPLE 9 (Moderate-level PA)

Enzymatically-processed lecithin used in formulation preparations similar to Example 3 were employed using Lipogen PAS15F (a PS and PA product produced by transphosphatidylation with lecithin and phospholipase D as described above from Lipogen Products (9000) Ltd.), to produce a moderate-level PA, suitable, and stable dairy formulation. A representative PL profile (weight fraction) based on $^{31}$P-NMR spectral data for the PL-fortified milk included: PA at 15% with the remainder being other PLs.

While the present invention has been described with respect to a limited number of embodiments, it will be appreciated that many variations, modifications, and other applications of the present invention may be made.

What is claimed is:

1. A process for the preparation of phospholipid-enriched (PL-enriched) dairy products as nutraceuticals for the formulation of functional foods, the process comprising the steps of:
   (a) combining a non-dairy-based PL-containing material, having phosphatidylserine (PS) in said PL-containing material, wherein said PS is derived in part from an enzymatically-processed lecithin as a PS-calcium and/ or -magnesium salt via transphosphatidylation with phospholipase D in the presence of L-serine and a calcium and/or magnesium salt, with water and an oil component to form a paste;
   (b) removing an excess amount of said water from said paste to form a PL-oil solution having a residual amount of said water; and
   (c) mixing said PL-oil solution with a dairy component, thereby obtaining a PL-enriched dairy product.

2. The process of claim 1, wherein said PL-enriched dairy product has the form of at least one nutraceutical type selected from the group consisting of: a medication, a medical food, a medical drink, a functional food, a functional drink, a nutritional supplement, a pharmaceutical supplement, and a dietary supplement.

3. The process of claim 1, wherein said PL-containing material includes at least one material selected from the group consisting of: a vegetal-derived lecithin, a non-vegetal-derived lecithin, a de-oiled lecithin, a native lecithin-oil solution, and an enzymatically-processed lecithin.

4. The process of claim 1, wherein said oil component includes at least one material selected from the group consisting of: a carrier oil and a native oil fraction from a lecithin production process.

5. The process of claim 1, wherein said step of combining is performed at a weight-to-weight (w-w) concentration of at least about 2% of said water to said PL-containing material.

6. The process of claim 1, wherein said step of removing is performed by at least one process selected from the group consisting of: a heating procedure, a vacuum-distillation procedure, and a solvent-based phase-separation procedure.

7. The process of claim 1, wherein said PL-oil solution has a weight-to-weight (w-w) concentration of at least about 0.01% of said residual amount of said water to said PL-containing material.

8. The process of claim 1, wherein said PL-oil solution has a weight-to-weight (w-w) concentration of about 10-80% of said PL-containing material to said oil component.

9. The process of claim 1, wherein said step of mixing includes at least one process selected from the group consisting of: a stirring procedure, a homogenizing procedure, and a pasteurizing procedure.

10. The process of claim 1, wherein said PL-enriched dairy product has a weight-to-weight (w-w) concentration of up to about 50% of said PL-oil solution to said dairy component.

11. The process of claim 1, wherein said PL-enriched dairy product is used in at least one product form selected from the group consisting of: a milk product, a chocolate product, a milk-ingredient supplemented product, an ice cream, a drink, a yoghurt, a processed cheese, a cottage cheese, a spread, a powdered dairy product, and a nutritional bar.

12. The process of claim 1, wherein a PS concentration of said PS is at least about 10% weight-to-weight (w-w) out of said PL-containing material.

13. The process of claim 12, wherein said PS concentration is up to about 86% weight-to-weight (w-w) out of said PL-containing material.

* * * * *